(12) United States Patent
Diaz et al.

(10) Patent No.: US 7,078,544 B2
(45) Date of Patent: Jul. 18, 2006

(54) PROCESS FOR PRODUCING STEROL OR STANOL ESTERS BY ENZYMATIC TRANSESTERIFICATION IN SOLVENT AND WATER FREE MEDIA

(75) Inventors: Miguel Angel Fuenzalida Diaz, Santiago (CL); Alejandro Markovits Rojas, Santiago (CL); Endre Markovits Schersl, Santiago (CL); Irene Martinez Basterrechea, Santiago (CL)

(73) Assignee: Harting, S.A., Santiago (CL)

( * ) Notice: Subject to any disclaimer, the term of this patent is extended or adjusted under 35 U.S.C. 154(b) by 304 days.

(21) Appl. No.: 10/205,964

(22) Filed: Jul. 26, 2002

(65) Prior Publication Data

US 2003/0092096 A1    May 15, 2003

(30) Foreign Application Priority Data

Aug. 22, 2001   (CL) .................................. 2044-2001

(51) Int. Cl.
*C07J 9/00* (2006.01)
*C12P 33/00* (2006.01)

(52) U.S. Cl. .................... 552/544; 552/545; 435/52

(58) Field of Classification Search ................ 552/544, 552/545; 435/52
See application file for complete search history.

(56) References Cited

U.S. PATENT DOCUMENTS 5,219,733 A  *  6/1993  Myojo et al. .................. 435/52
5,962,624 A  *  10/1999  Vonderhagen et al. ...... 528/274

FOREIGN PATENT DOCUMENTS

| JP | 01-040388 | * | 2/2001 |
| WO | WO 01/53511 | * | 7/2001 |

* cited by examiner

*Primary Examiner*—Barbara P. Badio
(74) *Attorney, Agent, or Firm*—Baker & McKenzie LLP

(57) ABSTRACT

A process for producing steryl or stanyl esters, comprises the steps of:
a) forming a reacting mixture by contacting a lipase with a reactant mixture wherein the reactant mixture comprise sterols or stanols and one or more esters selected from the group consisting of esters of a fatty acid with a short chain aliphatic alcohol;
b) separating the lipase from the reacting mixture to form a reacted mixture; and
c) separating steryl or stanyl esters from the reacted mixture.

The reaction is carried out in stirred reactors at pressures below atmospheric pressure and temperatures from 30 to 90° C. The separation of esters from the reacted mixtures is carried out by distillation at low pressures.

A process for esterifying sterols or stanols comprise forming a reacting mixture by contacting a lipase with a reactant mixture wherein the reactant mixture comprise sterols or stanols and one or more esters selected from the group consisting of esters of a fatty acid with a short chain aliphatic alcohol. The reaction of esterification is carried out in stirred reactors at pressures below atmospheric pressure and temperatures from 30 to 90° C.

17 Claims, 1 Drawing Sheet

PROCESS FOR PRODUCING STEROL OR STANOL ESTERS BY ENZYMATIC TRANSESTERIFICATION IN SOLVENT AND WATER FREE MEDIA

BACKGROUND AND SUMMARY OF THE INVENTION

The present invention relates to a process for transesterifying sterols or stanols in solvent free media and to a process for producing steryl or stanyl esters by enzymatic transesterification of sterols in solvent free media.

Steryl and stanyl esters are useful cholesterol lowering agents and as such are in high demand currently as nutraceutical food ingredients (*Food Technology*, 2001, 55, 1 pp. 59–67). Steryl and stanyl esters can be made by organic synthesis using different catalysts as disclosed in U.S. Pat. No. 6,184,397. The many disadvantages of organic synthesis is discussed in U.S. Pat. No. 5,219,733 which discloses a process for the enzymatic esterification or transesterification of sterols with fatty acids or with fatty acid esters in an aqueous media or in media containing water saturated organic solvent.

Nevertheless, the disclosed process also suffers from many setbacks. The presence of free water in the reacting mixture may favor hydrolysis over synthesis as can be noticed from the figures shown in the examples, and additionally there are lipases which do not exhibit any activity in water saturated organic solvents. (Yokozeki et al., European J. Appl. Microbiol. Biotechnol., 1982, 14, 1–5). On the other hand, the utilization of organic solvents may not be compatible with the elaboration of nutraceutical food ingredients.

The present invention discloses a novel and high efficiency esterifying process, not only of sterols, but stanols as well, in media without any free water or organic solvent, making the esterifyed products particularly suitable for nutraceutical uses.

In the present invention, it has been observed that certain microbial lipases exhibit transesterifying action on sterols and stanols or on mixtures of these compounds in a reacting system with absence of any organic solvent and free water.

The reacting system is formed when the lipase is contacted with a reactant mixture comprising sterols, stanols, and one or more components selected from the group consisting of fatty acids esterifyed with short chain aliphatic alcohols.

Lipase in the present invention means any formulation expressing transesterifying activity in the absence of free water or organic solvents, and may comprise one or more compounds derived from a fermentation broth of a microorganism or one or more compounds derived from a cellular extract of a microorganism. In these cases the formulation is called free lipase. Alternatively, the formulation may comprise an inert solid immobilizing one or more compounds derived from a fermentation broth of a microorganism or an inert solid immobilizing one or more compounds derived from a cellular extract of a microorganism. In latter cases the formulation is called immobilized lipase. Compounds derived from a fermentation broth or compounds derived from a cellular extract of bacteria of the genus *Pseudomonas* like *Pseudomonas stutzeri* or *Pseudomonas* (*Burkholderia*) *cepacia* are suitable for elaborating lipases either free or immobilized.

A lipolytic unit is the amount of formulation that liberates 1 micromole of fatty acid per minute at 37° C. from olive oil emulsified in presence of polyvinyl alcohol. The method for determining lipolytic activity used in the present invention is described in U.S. Pat. No. 5,219,733, being a standard technique for measuring lipolytic activity. It has been observed that there is a correlation between hydrolytic and transesterifying activities of the lipases utilized in the present invention.

The reaction can be carried out in presence either of a stoichiometric amount or stoichometric excess of esters of the fatty acid esters.

Transesterification reaction in the reacting mixture is carried out preferably in agitated reactors at pressures below atmospheric pressure, preferably below 300 mbar and at temperatures ranging from 30 and 90° C.

Fatty acids whose esters are useful for transesterifying sterols or stanols may be derived from an edible oil such as rapeseed oil, soybean oil, cottonseed oil, sunflower oil, palm oil, fish oil, and also may comprise fatty acids from 2 to 14 carbon atoms per molecule. These fatty acids can be esterified with a short chain aliphatic alcohol such as methanol, ethanol, propanol or buthanol in presence of sulfuric acid as catalyst, and utilized as transesterifying agents.

Sterols or stanols derived from the residue of the degumming of edible oils such as soy bean oil, sunflower oil, maize germ oil, palm oil, rapeseed oil or the so called wood alcohols which are mixtures of sterols and stanols derived black liquor soaps from Kraft cellulose pulping process, tall oil, or the residue of tall oil distillation known as tall oil pitch, are suitable for the transesterification process disclosed.

In order to finalize the reaction, the lipase is separated from the reacting mixture by either settling, filtering, centrifuging or by any suitable techniques. The resulting reacted mixture comprises steryl or stanyl esters of fatty acids. If stoichiometric excess of esters of fatty acids is used in the transesterifying reaction, the reacted mixture will comprise as well non-reacted excess of these esters. If desired, said excess of esters can be removed from the reacted mixture by distillation at reduced pressure as described in Example 7.

According to what has been disclosed, the process for producing steryl or stanyl esters comprises the steps of:

a) forming a reacting mixture by contacting a lipase with a reactant mixture wherein the reactant mixture comprise sterols or stanols and one or more esters selected from the group consisting of esters of a fatty acid with a short chain aliphatic alcohol;

b) separating the lipase from the reacting mixture to form a reacted mixture; and c) separating steryl or stanyl esters from the reacted mixture.

Furthermore, a process for the transesterification of sterols or stanols comprises forming a reacting mixture by contacting a lipase with a reactant mixture wherein the reactant mixture comprise sterols or stanols and one or more esters selected from the group consisting of esters of a fatty acid with a short chain aliphatic alcohol.

DETAILED DESCRIPTION OF THE INVENTION

Figure 1:
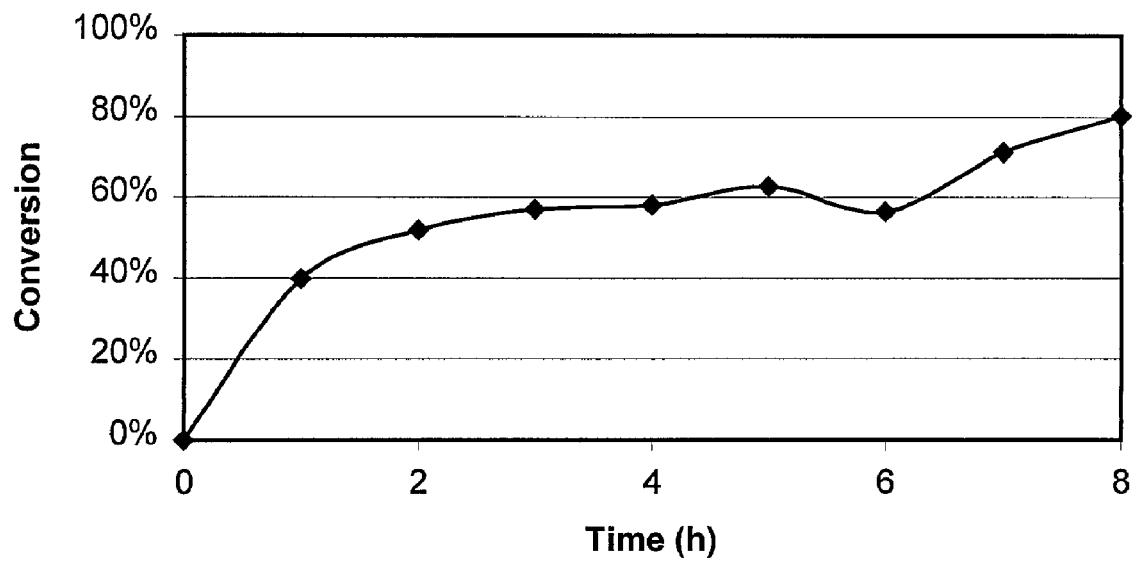
FIG. 1 is a graph showing the variation of the composition of the reacted mixture of Example 2.

The following examples illustrate ways for practicing the present invention:

EXAMPLE 1

Preparation of Ethyl Ester of Fatty Acids of Sunflower Oil 10 l technical grade ethanol, 313 g concentrated sulfuric acid and 10.3 Kg commercial sunflower oil fatty acids were loaded under slight nitrogen flux in a 40 l stainless steel agitated reactor provided with electrical heater, refrigeration coil, loading funnel, column, condenser, Dean-Stark separator, bottom valve, nitrogen injector and vacuum connection for distillation at reduced pressure. Nitrogen flux was interrupted and the mixture was refluxed at 77° C. for 10 hours with periodically monitoring the acid number. When the acid number reached 6.4, ethanol was distilled off until 90% of the initial amount of ethanol was recovered. The mixture was cooled to 60° C. and diluted with 7 kg of hexane. Remaining acidity was neutralized with 8 kg of an aqueous solution of technical grade sodium carbonate at 10%. The aqueous phase was eliminated and the organic phase was washed three times with 1 Kg of a water:ethanol mixture (1:1) to pH of 6.8. The neutral organic phase was desolventized at 95° C. and 25 mbar. Finally, 9.64 Kg of ethyl esters of fatty acids of sunflower oil were obtained.

EXAMPLE 2

Transesterification of a Mixture of Sterols and Stanols

A reacting mixture of the composition shown in Table 1 (initial composition at time=0) was formed by mixing 1000 ml of ethyl esters of fatty acids of sunflower oil, 180 g of a mixture of sterols and stanols (wood alcohols) and 10 g of lipase of *Pseudomonas stutzeri* (MEITO SANGYO CO., LTD. Lipase-TL) with lipolytic activity of 20,000 units per gram, were loaded in a 2000-ml SCHOTT-DURAN round bottom, flat flange reaction vessel with flat flange lid provided with 4 standard ground necks. The reactor was partially immersed in a water bath at 60° C. A reactor outlet was connected to a vacuum pump (TRIVAC B D 16B) keeping the pressure at 2 mbar in the reactor during the reaction. Stirring was made by means of a magnetic stirrer. The agitation was stopped every hour to allow for the taking of a sample, the sample was centrifuged at 10,000 g for 15 minutes to remove lipase, and the sterol and stanol content of the centrifuged sample was measured.

Analysis of free stanols and sterols was carried out using a Hewlett-Packard HP 6890 series 2 chromatograph provided with a HP-5 capillary column of 30-m long, 0.32-mm diameter and 0.25-mm film. Oven temperature was 300° C., injector and detector temperature was 320° C., carrier helium flux was was 0.92 ml/min with 60:1 split and 15-minute program. The details of the analysis are disclosed in Chilean Patent Application No. 85/98.

Table 1 shows the variation of the composition of the reacted mixture at different reacting times.

TABLE 1

Variation of the composition of the reacted mixture at different reaction times of Example 2

| | Time (h) | | | | | | | | |
|---|---|---|---|---|---|---|---|---|---|
| | 0 | 1 | 2 | 3 | 4 | 5 | 6 | 7 | 8 |
| Component | % in weight of component in the mixture | | | | | | | | |
| Campesterol | 1.05 | 0.58 | 0.47 | 0.42 | 0.44 | 0.38 | 0.43 | 0.29 | 0.22 |
| Campestanol | 0.12 | 0.00 | 0.00 | 0.00 | 0.00 | 0.00 | 0.00 | 0.00 | 0.00 |
| Sitosterol | 9.79 | 6.08 | 4.85 | 4.33 | 4.27 | 3.82 | 4.49 | 2.96 | 2.05 |
| Sitostanol | 2.22 | 1.11 | 0.89 | 0.77 | 0.69 | 0.57 | 0.59 | 0.44 | 0.26 |
| Total wood alcohols | 13.18 | 7.77 | 6.20 | 5.52 | 5.39 | 4.77 | 5.52 | 3.70 | 2.53 |

FIG. 1 shows the conversion kinetics of the transesterification of wood alcohols to the corresponding fatty esters. Conversion of wood alcohols to fatty esters ($X_{alcohols}$) is calculated by means of the following expression:

$$X_{alcohols} = (C_{0alcohols} - C_{acohols})/C_{0alcohols}$$

Where:

$C_{0alcohols}$ is the concentration of sterols and stanols in the reactant mixture $C_{alcohols}$ is the concentration of sterols and stanols in the reacted mixture FIG. 1: Variation of the composition of the reacted mixture of Example 2

EXAMPLE 3

Transesterification of Wood Alcohols

Figure 2:
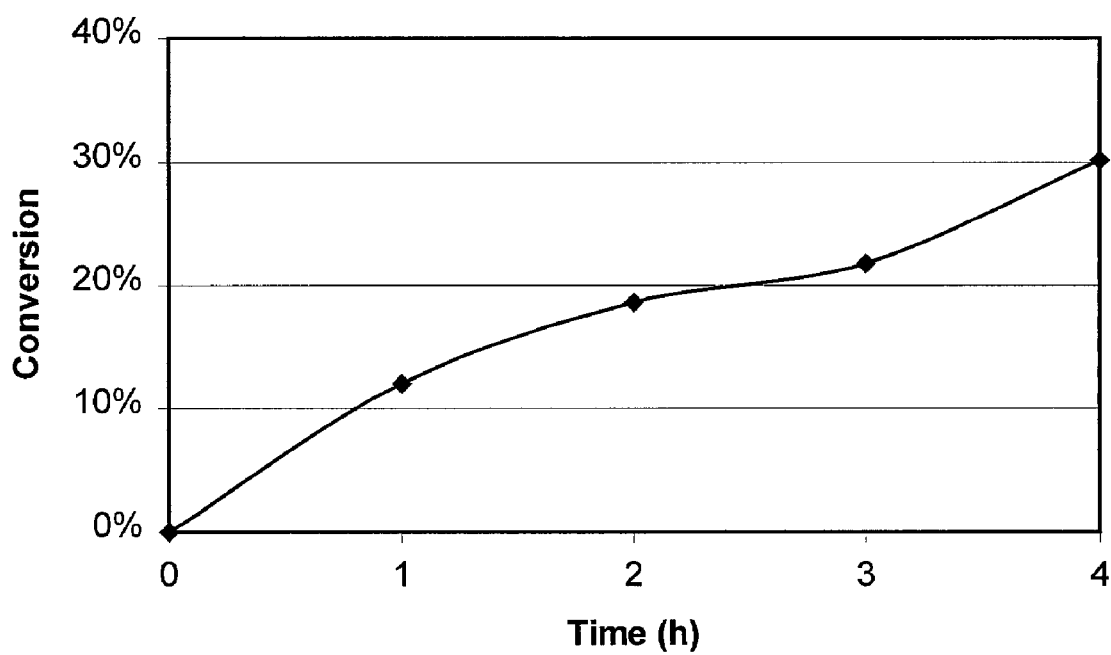
FIG. 2 is a graph showing the variation of the composition of the reacted mixture of Example 3.

A reacting mixture, whose composition is shown in Table 2, was formed by mixing 100 ml of ethyl esters of fatty acids of tall oil, prepared as described in Example 1, were mixed in the reactor of Example 2 with 10 g of wood alcohol and 0.5 g of lipase of *Pseudomonas* (*Burkholderia*) *capacia* (MEITO SANGYO CO., LTD Lipase-SL) with lipolytic activity of 36,000 units per gram. Reaction temperature was 70° C. and the pressure 0.8 mbar. Extraction of samples and analysis were performed as described in Example 2. Table 2 shows the variation of the composition of the reacted mixture with time and FIG. 2 shows the variation at different reaction times of the conversion in the reacted mixture of wood alcohols to steryl and stanyl esters.

TABLE 2

Variation of the composition of the reacted mixture
at different reaction times in Example 2

| Component | Time (h) | | | | |
|---|---|---|---|---|---|
| | 0 | 1 | 2 | 3 | 4 |
| | % in weight of component of the mixture | | | | |
| Campesterol | 0.76 | 0.67 | 0.63 | 0.60 | 0.54 |
| Campestanol | 0.06 | 0.05 | 0.04 | 0.04 | 0.03 |
| Sitosterol | 7.19 | 6.41 | 6.02 | 5.86 | 5.28 |
| Sitostanol | 1.25 | 1.02 | 0.85 | 0.75 | 0.62 |
| Total wood sterols | 9.26 | 8.15 | 7.55 | 7.25 | 6.47 |

FIG. 2: Variation of the composition of the reacted mixture of Example 3.

EXAMPLE 4

Immobilization of Lipase in Celite

Lipase of *Pseudomonas stutzeri* PL-836 (MEITO SANGYO CO., LTD. Lipase-TL) with lipolytic activity of 45,000 units per gram was immobilized in Celite by adsorption and also trapping of the adsorbed enzyme in a polymeric resin according to the method of Yokokezi et al (European J. Appl. Microbiol. Biotechnol., 1982, 14, 1–5), resulting a catalyst with lipolytic activity of 25,000 and 32,000 units per gram respectively of immobilized lipase.

EXAMPLE 5–6

Transesterification with Immobilized Lipase 15 g of sterols and 15 g of stanols were separately transesterifyed, as described in Example 2, with 0.5 g of lipase of *Pseudomonas stutzeri* PL-836 (MEITO SANGYO CO., LTD. Lipase- TL) immobilized by adsorption in Celite, with 100 ml of ethyl esters of fatty acids of sunflower oil. Table 3 shows reaction conditions and results of the respective conversions reached after 6 hours of reaction. The analysis of samples was carried out as described in Example 2.

TABLE 3

Results of Examples 5 and 6

| | Example | % in weight | T ° C. | P mbar | Conversion |
|---|---|---|---|---|---|
| Sterols | 5 | 14.7 | 45 | 15 | 0.66 |
| Stanols | 6 | 14.7 | 45 | 15 | 0.71 |

Where:
% in weight is percentage in weight of sterols or stanols in the reactant mixture
T, reaction temperature (C°).
P, pressure in reactor (mbar).

EXAMPLE 7

Separation of Non-Reacted Ethyl Esters of Fatty Acids of Sunflower Oil

A reacting mixture made according to Example 3 was filtered obtaining 978.5 g of lipase free reacted mixture. The reacted mixture was distilled at 10 mbar in an UIC KDL 4 short path distillation column, with temperatures of the heated surface and the internal condenser at 170 and 30° C. respectively. 622.7 g of distillate was collected at the internal condenser comprising non-reacted ethyl esters of fatty acids of sunflower oil, and 352.8 g of residue was collected at the bottom of the heated surface comprosing 16% in weight of wood alcohols.

What is claimed is:

1. A process for preparing a mixture of sterol and stanol esters, the process comprising the steps of: reacting a mixture of sterols and stanols consisting essentially of campesterol, campestanol, sitosterol and sitostanol with one or more components selected from the group of fatty acid esters of short chain aliphatic alcohols, in contact with a lipase derived from the microorganism *Pseudomonas stutzeri*.

2. The process according to claim 1, wherein the lipase is derived from *Pseudomonas stutzeri* strain PL-836.

3. The process according to claims 1 or 2, wherein the short chain aliphatic alcohols are selected from the groups of methanol ethanol, and combinations thereof.

4. The process according to claims 3 wherein the reaction is carried out at a temperature of between about 30° and about 90° C. and at a pressure less than about 300 mbar.

5. The process according to claim 4, wherein the reaction is carried out in the absence of an organic solvent and in the absence of added water.

6. The process according to claim 5, wherein the fatty acid esters are present in a greater molar amount than the mixture of sterols and stanols.

7. The process according to claim 6, wherein the lipase is separated from the mixture resulting from the reaction thereby forming a reacted mixture free of lipase.

8. The process according to claim 7 wherein the reacted mixture is distilled thereby forming a mixture of sterol and stanol esters.

9. In a process for preparing sterol or stanol esters, the process comprising the steps of: reacting sterols or stanols with one or more components selected from the group of fatty acid esters of short chain aliphatic alcohols, in the absence of an organic solvent and added water in contact with a lipase derived from a microorganism, the improvement comprising that the lipase is derived from *Pseudomonas stutzeri*.

10. The process according to claim 9, wherein the lipase is derived from *Pseudomonas stutzeri* strain PL-836.

11. The process according to claims 9 or 10, wherein the short chain aliphatic alcohols are selected from the group of methanol ethanol, and combinations thereof.

12. The process according to claim 11, wherein the sterols or stanols are a mixture of campesterol, campestanol, sitosterol and sitostanol.

13. The process according to claims 12, wherein the reaction is carried out at a temperature of between about 30° and about 90° C. at a pressure less than about 300 mbar.

14. The process according to claim 13, wherein reaction is carried out in the absence of an organic solvent and added water.

15. The process according to claim 14, wherein the fatty acid esters are present in a greater molar amount than the mixture of sterols and stanols.

16. The process according to claim 15, wherein the lipase is separated from the mixture thereby resulting from the reaction, forming a reacted mixture free of lipase.

17. The process according to claim 16, wherein the reacted mixture is distilled thereby forming a mixture of sterol and stanol esters.

* * * * *